(12) United States Patent
Chanton et al.

(10) Patent No.: US 6,250,295 B1
(45) Date of Patent: Jun. 26, 2001

(54) TOOL

(75) Inventors: Marzell Chanton, St. Niklaus; Walter Linder, Etziken; Daniel Jeiziner, St. Niklaus; Raphael Chiesa, Zuchwil, all of (CH)

(73) Assignee: Scintilla AG, Solothurn (CH)

( * ) Notice: Subject to any disclaimer, the term of this patent is extended or adjusted under 35 U.S.C. 154(b) by 0 days.

(21) Appl. No.: 09/262,686

(22) Filed: Mar. 4, 1999

(30) Foreign Application Priority Data

Mar. 11, 1998 (DE) ............................................... 198 10 511

(51) Int. Cl.[7] ........................................................ B28D 1/04
(52) U.S. Cl. .......................... 125/15; 125/11.23; 125/20; 451/21; 451/542; 116/208
(58) Field of Search .................................... 125/11.23, 20, 125/115; 451/21, 542; 116/208

(56) References Cited

U.S. PATENT DOCUMENTS

| | | | |
|---|---|---|---|
| 2,562,833 | * | 7/1951 | True ..................................... 116/208 |
| 2,580,860 | * | 1/1952 | Stokes .................................. 116/206 |
| 3,863,401 | * | 2/1975 | Schwarzkopt et al. ............. 451/542 |
| 3,964,211 | * | 6/1976 | Engle ..................................... 451/21 |
| 4,473,125 | * | 9/1984 | Addudle et al. ..................... 175/410 |
| 4,860,722 | * | 8/1989 | Veglio ................................... 125/15 |
| 4,886,009 | | 12/1989 | Gondar et al. . |
| 4,926,950 | * | 5/1990 | Zijsling ................................. 175/39 |
| 5,392,759 | | 2/1995 | Kwang . |
| 5,433,187 | * | 7/1995 | Hayasaka et al. ..................... 125/15 |
| 6,073,711 | * | 7/2000 | Ingmarsson ........................ 175/420.2 |

FOREIGN PATENT DOCUMENTS

| | | | |
|---|---|---|---|
| 0 514 822 B1 | | 8/1995 | (EP) . |
| 1164350 | | 9/1969 | (GB) . |
| 1 390 825 | | 4/1975 | (GB) . |
| 0138237 | * | 4/1985 | (IT) ........................................ 125/15 |
| 0142076 | * | 6/1986 | (JP) ........................................ 125/15 |
| WO 95/22446 | | 8/1995 | (WO) . |

OTHER PUBLICATIONS

WPI Abstract Accession No. 96–059150/23 Andde 44 24 203 A1.

* cited by examiner

Primary Examiner—Joseph J. Hail, III
Assistant Examiner—George Nguyen
(74) Attorney, Agent, or Firm—Michael J. Striker

(57) ABSTRACT

A tool for treatment of rock, masonry or concrete by drilling, grinding or cutting off, the tool has a plurality of cutting segments each having a plurality of bonded cutting bodies formed as diamond crystals and subjected to an abrasive wear during an operation, a tool base body which carries the cutting segments, and at least one marking provided on at least one segment and forming a wear indicator, the at least one marking being arranged so that it changes during operation of the tool with wear of the cutting segments.

5 Claims, 3 Drawing Sheets

US 6,250,295 B1

TOOL

BACKGROUND OF THE INVENTION

The present invention generally relates to tools. More particularly, it relates to a tool which is used for treatment of rock, masonry or concrete.

A tool, in particular for treatment of rock, masonry or concrete is disclosed for example in the European patent document EP-B-514 822 and formed as a rock drill. The rock drill is provided with eight cutting segments which are distributed over the periphery and composed of a plurality of bonded cutting bodies, in particular diamond crystals. During the working operations they are subjected to material-removing wear. The cutting segments are mounted on a tool base body. In order to differentiate different types of cutting segments, marks are provided in the cutting segments. They distinguish from the binding medium of the corresponding cutting segment by color and during a corresponding application of the tool can not be lost.

SUMMARY OF THE INVENTION

Accordingly, it is an object of the present invention to provide a tool of the above mentioned general type, in which the use condition of the tool can be determined in a simple manner without comparison with other, non-used tools.

In keeping with these objects and with others which will become apparent herein after, one feature president invention resides, briefly stated, in a tool, in particular for treatment of rock, masonry or concrete, for example by drilling, grinding or cutting off, which has a plurality of cutting segments composed of a plurality of bonded cutting grains such as diamond crystals and subjected during the operation to a material-removing wear, and which also has a tool base body which carries the cutting segments, wherein in accordance with the present invention at least one cutting segment has at least one mark which serves as a wear indicator for the tool, in that the at least one marking is arranged so that its appearance or property or its relative length to cutting surface of the cutting segment change during the use of the tool as a result of the wear.

When the tool is designed in accordance with the present invention, it provides for the above mentioned highly advantageous results.

In accordance with another feature of the present invention, the marking can be formed as an indicator provided on the tool and formed and as a scale with associated value data. It can be arranged at least partially on the tool base body, and applied after the production of the cutting segments on the tool, for example by a laser treatment. On the other hand, the mark can be also applied on the cutting segment during the manufacture of the tool.

In accordance with another feature of the present invention, the marking can be formed as at least one intermediate member provided in at least one cutting segment and having a cross-section which is changeable in the abrasion direction of the cutting segment. The intermediate member can be different from the cutting segment by color.

Also, the marking can be formed by differently deep axial notches in the outer periphery of the cutting segments, by several axial throughgoing openings in the cutting segment, by lines, etc.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
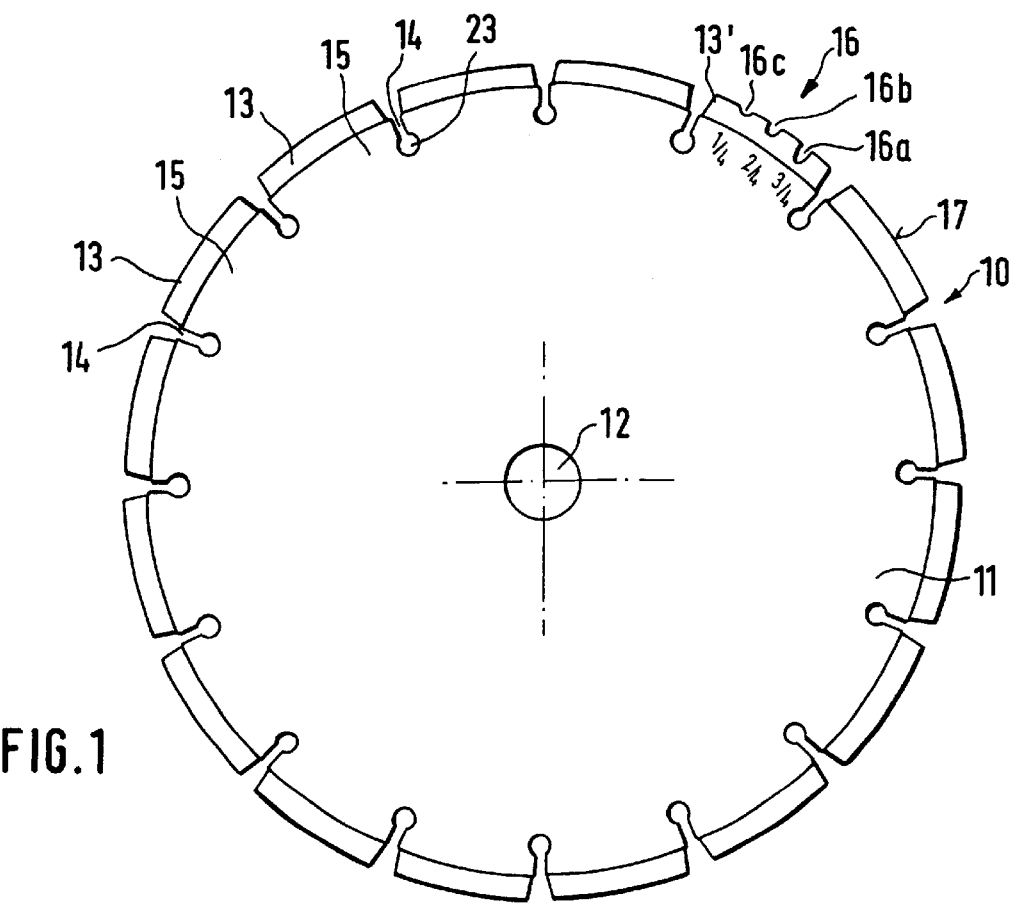
FIGS. 1–6 are views showing tools which are formed as cutting off disks and are provided with various markings for determination of a wear condition of the tool, in accordance with the present invention.

A tool in accordance with the present invention, which is disclosed in this application as an example, can be formed as a cutting off disk 10 shown in FIG. 1. The cutting off disk has a tool base body 11 which has a substantially disk-shaped construction. The tool base body 11 has a central mounting hole 12 for mounting of the cutting off disk 10 on the drive shaft of a not shown angular grinder.

The cutting off disk 10 is provided with a plurality of cutting segments 13 which are arranged on its outer periphery and uniformly distributed over it. The cutting segments 13 each have a plurality of cutting grains, in particular diamond crystals which are bound by means of a suitable binder. The binder for the inventive cutting off disk can be for example a metal alloy, such as bronze. It is mixed in a powder form with the cutting grains and thereafter is sintered. The cutting segments 13 are mounted each on a supporting piece 15 of the base body 11. The neighboring supporting pieces 15 are separated from one another by a radially outwardly open slot 14. For preventing a notch action, the slots 14 are provided at their inner ends with circular passages 23.

The cutting segments 13 during the use of the cutting off disk 10 are subjected to abrasive wear. In other words, with the increased use of the cutting off disk 10 they become smaller. In order to determine the wear condition of the cutting segments 13, in this embodiment the cutting segment 13' is provided with three markings 16. The markings 16 are formed as axial notches which are provided on the outer periphery of the cutting segments 13' and have different depths. A first notch 16a has a radial depth which extends over substantially three quarters of the radial thickness of the cutting segment 13'. A second notch 16b extends over substantially the half of the radial thickness of the cutting segment 13'. A third notch 16c extends over substantially a quarter of the radial thickness of the cutting segment 13'.

During the use of the cutting segments 13, 13' over their service life, they are subjected to abrasion or wear, by which the dimensions of the notches 16a, 16b, 16c and thereby the appearance of the markings 16 are changed. With the increased wear, the relative length of the markings 16 to a cutting surface 17 of the cutting segments 13, 13' changes. With increased wear the notches 16a, 16b, 16c become smaller, until approximately at three quarters of the maximum thickness of the cutting segments 13, 13', the notches 16a, 16b, 16c are completely removed.

The markings 16 with the notches 16a, 16b, 16c are applied preferably during the production of the cutting segments 13 in the cutting surface 17 of the cutting segment 13'. This can be performed for example by a laser treatment. In addition to the markings 16, an indicator 24 formed as a scale can be provided on an end side of the tool base body 11 by means of laser engraving. The scale can have value data, such as for example one quarter, two quarters, three quarters, etc., which are associated with the corresponding notches 16a, 16b, 16c.

Figure 2:
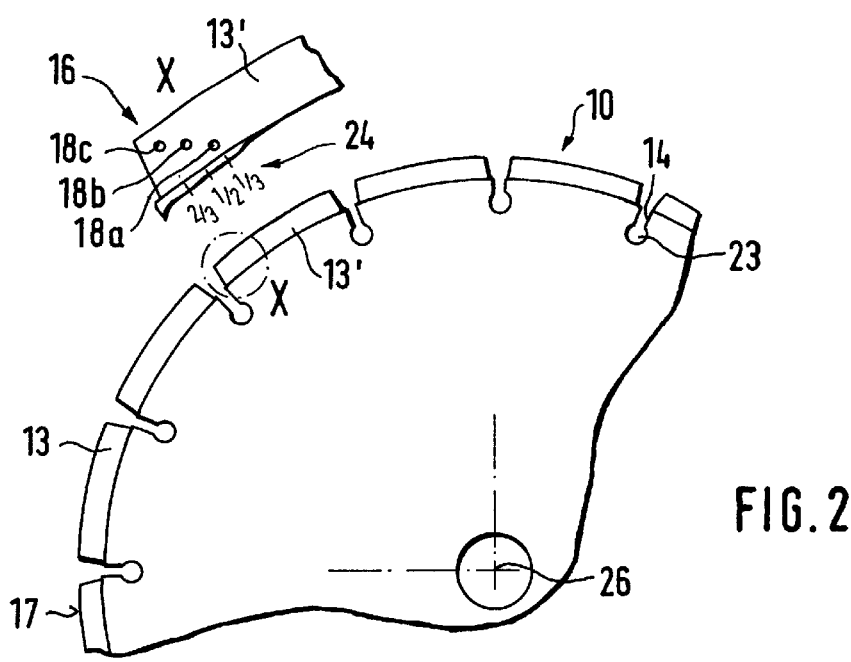

FIG. 2 shows a second embodiment of the tool in accordance with the present invention. Same or similar parts of this embodiment are identified with the same reference numerals.

In FIG. 2 the cut off disk 10 also has a plurality of cutting segments 13 with a special segment 13' provided with the markings 16. The markings 16 here are formed as axial openings 18a, 18b, 18c which are located in the region X of the cutting segment 13' shown on an enlarged scale in FIG. 2a. The openings 18a, 18b, 18c have different radial distances from a central axis 26 of the cutting off disk 10. The openings 18a, 18b, 18c open at the end side of the cutting segment 13' and thereby are easy to observe. With increased wear of the cutting segment 13', the relative position of the openings 18a, 18b, 18c to the cutting surface 17 changes. The openings 18a, 18b, 18c become closer to the cutting surface 17 when the surrounding material is removed during the operation. As can be seen from FIG. 2, in this embodiment also an indicator 24 with a scale is provided.

Figure 3:
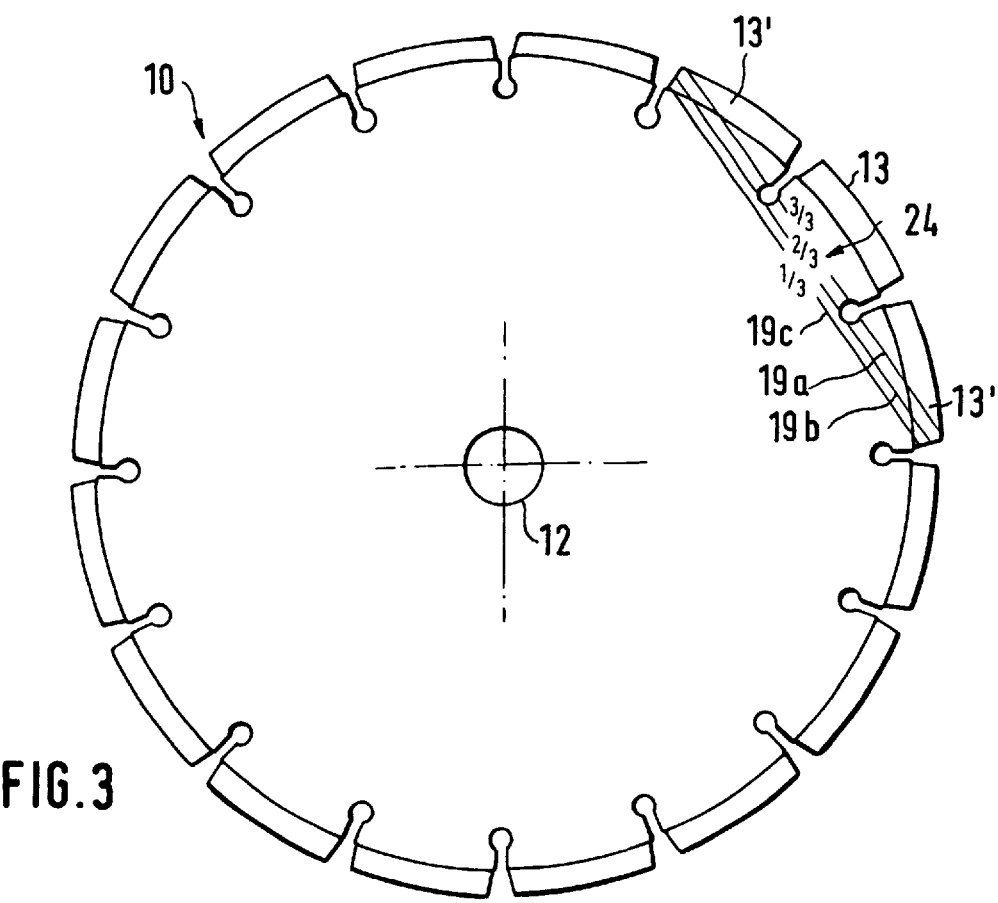

FIG. 3 shows the tool in which the markings 16 are formed by lines 19a, 19b, 19c. The lines extend substantially parallel to a tangent to the outer periphery of the tool 10 and are laterally open on different cutting segments 13' at different radial distances from the central axis 26. The lines 19a, 19b, 19c extend partially on the tool base body 11, on which also the scale 24 is provided. The wear condition is therefore determined by the position of the corresponding intersection point of the cutting surface 17 and the lines 19.

Figure 4:
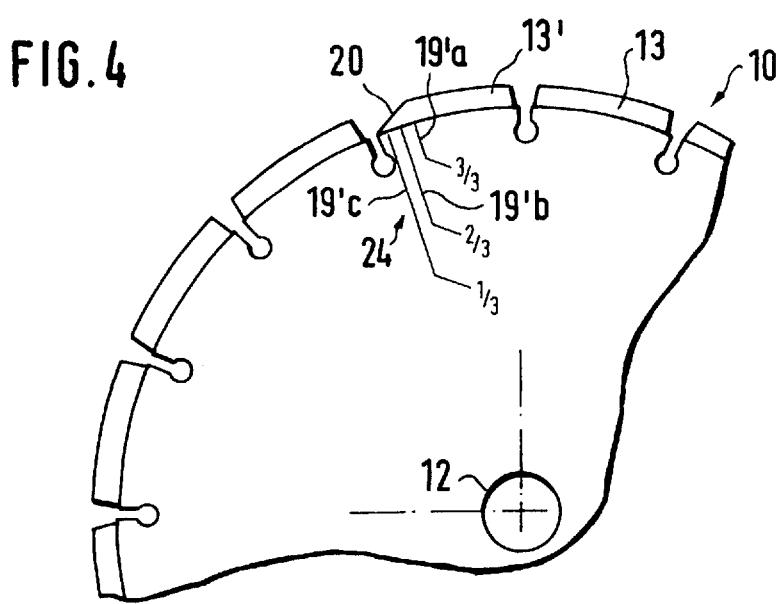

FIG. 4 shows another embodiment of the tool in accordance with the present invention. Here the cutting segments 13' which carries the marking 16 has an incline 20 in a peripheral direction. Its length forms a value for the wear condition of the tool 10. The indicator 24 is formed by parallel, radially extending lines 19. Corresponding value data are associated with the lines.

Figure 5:
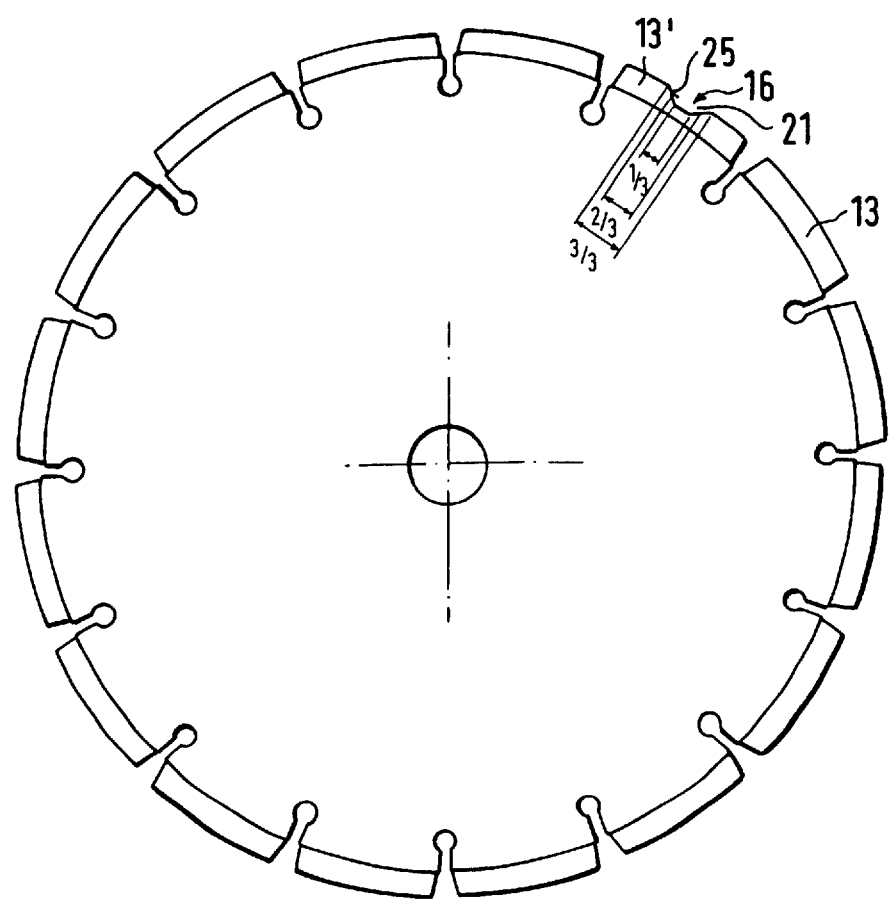
Figure 6:
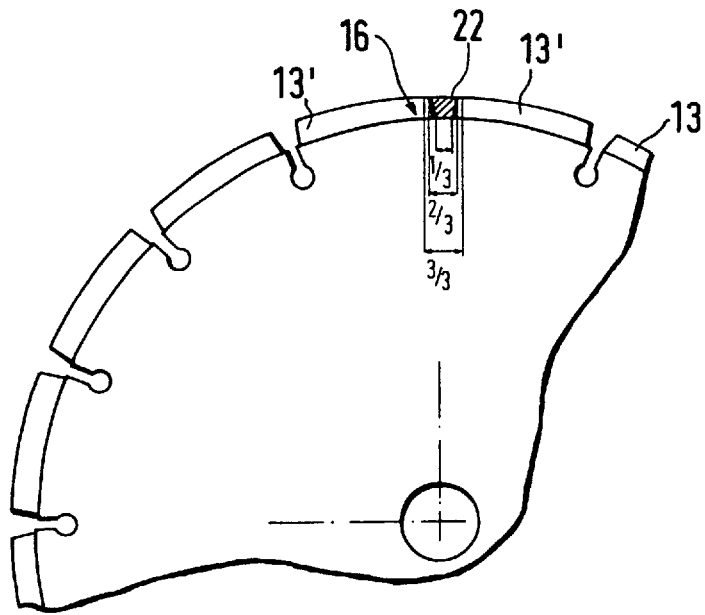

FIG. 5 shows a tool in accordance with still another embodiment of the present invention, in which the markings 16 are arranged in the center of the segment 13' and formed by a single, wide notch 21 having lateral inclined surfaces 25. The size of the notch 21 with the inclined surfaces 25 represents a value for the wear condition of the tool 10. The indicator 24 is formed by a pair of lines 25 which have a different parallel distance and end in the region of the notch 21.

Finally, the tool in accordance with the embodiment of FIG. 1 has the marking 16 which is arranged between two neighboring cutting segments 13'. The marking 16 has an intermediate member 22 which is conical in a radial direction and has a composition different from the material of the cutting segment 13. With increased wear the cross-section of the marking 16 is reduced. The intermediate member 22 can be designed for example in color, so that it is different from the cutting segments 13'. The intermediate member 22 can be also integrated in one of the cutting segments 13'.

It will be understood that each of the elements described above, or two or more together, may also find a useful application in other types of constructions differing from the types described above.

While the invention has been illustrated and described as embodied in tool, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

What is claimed is:

1. A tool, comprising a tool base body; and a plurality of cutting segments provided on said tool base body, said cutting segments each having a plurality of bonded cutting bodies and subjected during use to an abrasive wear; at least one of said cutting segments being provided with a plurality of openings arranged at definite different radial distances from a central axis of the tool so as to form a wear indicator, so that when due to wear a corresponding one of said openings is reached, a definite radial distance of said corresponding opening from said central axis indicates a wear value of said at least one cutting segment and therefore of the tool.

2. A tool as defined in claim 1, wherein said openings are formed by a plurality of axial notches which have different depths and are provided in an outer periphery of said at least one cutting segment.

3. A tool as defined in claim 1, wherein said openings are formed by a plurality of axially throughgoing openings which are formed in said at least one cutting segment and which are located at said different radial distances from said central axis of said tool.

4. A tool as defined in claim 1, wherein one of said cutting segments is provided with said openings, while all other cutting segments are devoid of said openings.

5. A tool, comprising a tool base body; and a plurality of cutting segments provided on said tool base body, said cutting segments each having a plurality of bonded cutting bodies and subjected during use to an abrasive wear; at least one of said cutting segments being provided with a plurality of openings arranged at definite different radial distances from a central axis of the tool so as to form a wear indicator, which is provided with a scale corresponding to the openings, so that when due to wear a corresponding one of said openings is reached, a definite radial distance of said corresponding opening from said central axis indicates a wear value of said at least one cutting segment and therefore of the tool.

* * * * *